US00PP23658P2

(12) United States Plant Patent
Stemkens

(10) Patent No.: US PP23,658 P2
(45) Date of Patent: Jun. 11, 2013

(54) ***VERBENA* PLANT NAMED 'VEAZ0008'**

(50) Latin Name: *Verbena×hybrida*
Varietal Denomination: VEAZ0008

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/317,197

(22) Filed: Oct. 11, 2011

(51) Int. Cl.
*A01H 5/00* (2006.01)

(52) U.S. Cl.
USPC ..... Plt./308

(58) Field of Classification Search ..... Plt./308
See application file for complete search history.

*Primary Examiner* — Kent L Bell
(74) *Attorney, Agent, or Firm* — Joshua L. Price

(57) ABSTRACT

A new *Verbena* plant named 'VEAZ0008' particularly distinguished by the white flowers, a compact and well branched habit, good floriferousness, dissected leaves and creeping and trailing growth.

1 Drawing Sheet

Latin name of the genus and species of the plant claimed: *Verbena×hybrida*.

Varietal denomination: 'VEAZ0008'.

BACKGROUND OF THE NEW PLANT

The present invention comprises a new *Verbena*, botanically known as *Verbena×hybrida*, and hereinafter referred to by the variety name 'VEAZ0008'.

'VEAZ0008' is a product of a planned breeding program. The new cultivar has white flowers, a compact and well branched habit, good floriferousness, dissected leaves and a creeping and trailing growth.

'VEAZ0008' originated from an open pollinated hybridization made in August 2006 in a controlled breeding environment in Enkhuizen, Netherlands. The female parent was the unpatented, proprietary plant designated 'E1086-2' with white flowers, less floriferousness and more vigorous growth.

The male parent of 'VEAZ0008' was an unknown plant. The resultant seed was sown in January 2007.

'VEAZ0008' was selected as one flowering plant within the progeny of the stated open pollination in May 2007 in a controlled environment in Enkhuizen, Netherlands.

The first act of asexual reproduction of 'VEAZ0008' was accomplished when vegetative cuttings were propagated from the initial selection in May 2007 in a controlled environment in Enkhuizen, Netherlands.

BRIEF SUMMARY OF INVENTION

Horticultural examination of plants grown from cuttings of the plant initiated in May 2007, and continuing thereafter, has demonstrated that the combination of characteristics as herein disclosed for 'VEAZ0008' are firmly fixed and are retained through successive generations of asexual reproduction.

'VEAZ0008' has not been observed under all possible environmental conditions. The phenotype may vary significantly with variations in environment such as temperature, light intensity and day length.

Plant Breeder's Rights for this cultivar were applied for in Canada on Dec. 24, 2010, #10-7148 and in the Community Plant Variety Office on Oct. 20, 2010, #2010/2236. 'VEAZ0008' has not been made publicly available more than one year prior to the filing of this application.

The following traits have been repeatedly observed and are determined to be basic characteristics of the new variety. The combination of these characteristics distinguishes this Verbena as a new and distinct variety.

BRIEF DESCRIPTION OF THE PHOTOGRAPHS

The accompanying photographic drawing shows typical flower and foliage characteristics of 'VEAZ0008' with colors being as true as possible with an illustration of this type. The photographic drawing shows a flowering potted plant of the new variety and a close-up of a flower.

DETAILED BOTANICAL DESCRIPTION

The aforementioned photographs were taken in April 2010 from plants grown in a greenhouse trial in Enkhuizen, The Netherlands. These plants were growing in 12 cm pots and were approximately 12 weeks of age. The close-up photograph was taken in April, 2011 in Gilroy California. Plants were about 9-11 weeks of age, grown in a greenhouse breeder's trial.

The plant descriptions and measurements were taken in May 2011 in Enkhuizen, Netherlands on about 13 week old plants that had been planted into 12 cm pots and were grown on benches in a greenhouse at a minimum temperature (heating temperature) of 12° C. From April on, a minimum night temperature of 8° C. was held, while day temperatures were much higher, depending on outdoor temperature.

Color references are made to The Royal Horticultural Society Colour Chart (R.H.S.) 2001.

TABLE 1

DIFFERENCES BETWEEN THE NEW VARIETY 'VEAZ0008' AND A SIMILAR VARIETY

| | 'VEAZ0008' | 'Ipwei' (U.S. Ser. No. 12/072,079, abandoned) |
|---|---|---|
| Plant vigor: | More compact | More vigorous |
| Flower size: | Larger | Smaller |
| Internode length: | Shorter | Longer |

Plant:

*Form, growth and habit*.—Herbaceous, initially compact and spreading, later becoming decumbent to trailing.

*Plant height*.—About 15.0 cm.

*Plant height* (*inflorescence included*).—About 25.0 cm.

*Plant width*.—About 29.0 cm.

Roots:

*Number of days to initiate and produce roots*.—About 10-14 days at about 22 degrees C.

*Type*.—Fine, fibrous, free branching.

*Color*.—RHS N155B.

Foliage:

*Arrangement*.—Opposite.

*Immature, leaf color, upper surface*.—RHS 137D. Lower surface: Between RHS 139C and RHS 139D.

*Mature, leaf color, upper surface*.—RHS 137A. Lower surface: RHS 137D.

*Length*.—About 3.0 cm.

*Width*.—2.5-3.0 cm.

*Shape*.—Pinnatifid.

*Base shape*.—Attenuate.

*Apex shape*.—Apiculate.

*Margin*.—Dissected.

*Texture, upper surface*.—Short hair. Lower surface: Short, stiff hair mainly along the veins; some glandular hairs.

*Color of veins, upper surface*.—RHS 137A.

*Color of veins, lower surface*.—RHS 144C.

*Petiole color*.—RHS 145B; with RHS 145C on the under side.

*Length*.—0.4-0.6 cm.

*Diameter*.—0.1-0.3 cm.

*Texture*.—Hirtellous.

Stem:

*Characteristics*.—Side branches develop potentially at every node.

*Color of stem*.—RHS 145A.

*Length of stem*.—Approximately 12.0-15.0 cm.

*Diameter*.—0.2 cm.

*Length of internodes*.—Up to 5.0 cm.

*Texture*.—Rough; densely covered with hair; hirsute.

*Color of peduncle*.—Between RHS 144A and RHS 144B.

*Length of peduncle*.—Most often 0.5-4.0 cm.

*Peduncle diameter*.—0.2 cm.

*Texture*.—Rough, densely covered with short glandular hair; hirtellous.

Inflorescence:

*Type*.—Umbel-like, but actually a spike, umbrella-shaped to roughly semi-spherical.

*Blooming habit*.—Flowers continuously.

*Quantity of inflorescences per plant*.—16-23.

*Lastingness of individual blooms on the plant*.—New florets continue to open in one spike over a period of approximately 14 days in the greenhouse.

*Fragrance*.—None.

*Inflorescence horizontal diameter*.—4.0 cm.

*Inflorescence depth* (*height*).—2.5 cm.

*Quantity of flowers and buds per inflorescence*.—40-45.

Bud (just when starting to show color):

*Color*.—Whiter than RHS 155D.

*Length*.—1.3 cm.

*Width*.—0.2 cm.

*Shape*.—Mainly tube-shaped with a bulbous end.

Floret:

*Form and type*.—Sessile; salverform, composed of 5 partly fused petals with a base of a narrow tube.

*Immature color, upper surface*.—Whiter than RHS 155D. Lower surface: Whiter than RHS 155D.

*Mature color, upper surface*.—Whiter than RHS 155D. Lower surface: Whiter than RHS 155D.

*Floret diameter*.—About 1.4 cm.

*Floret depth*.—1.3 cm.

*Length of petals*.—0.7 cm.

*Width of petals*.—0.7 cm.

*Petal shape*.—Obcordate.

*Apex shape*.—Emarginate.

*Margin*.—Entire.

*Petal texture, upper surface*.—Smooth and glabrous. Lower surface: Smooth and glabrous.

*Corolla tube length*.—1.4 cm.

*Corolla tube color inside*.—RHS 157B. Tube color outside: RHS 157B.

*Corolla texture, inside*.—Glabrous. Outside: Glabrous basally; glandular hairs at the flare.

Calyx:

*Type*.—Five sepals whose margins are fused to each other along their length, with a transparent membrane of less than 0.1 cm in width and with one smaller sepal attached to the base of the calyx.

*Color of sepals*.—RHS 143B.

*Length of sepals*.—0.8 cm.

*Width of sepals*.—0.15 cm.

*Sepal shape*.—Linear, fused.

*Apex shape*.—Acute.

*Margins*.—Entire.

*Texture*.—Densely covered with short hair.

Reproductive organs:

*Pistil*.—1.

*Length*.—1.2 cm.

*Style color*.—RHS 144D.

*Style length*.—1 cm.

*Stigma color*.—RHS 144A.

*Stamens*.—Anthers and filaments fused to upper half of corolla tube; four anthers with two pollen sacs per anther.

*Color of filaments*.—RHS 150D to RHD 155B.

*Length filaments*.—0.1 cm.

*Anther color*.—RHS 144D.

*Length of anthers*.—0.1-0.15 cm.

*Color of pollen*.—RHS 1A.

*Pollen amount*.—Little.

Fertility/seed set: Has not been observed on this hybrid.

Disease/pest resistance: Has not been observed on this hybrid.

What is claimed is:

1. A new and distinct variety of *Verbena* plant named 'VEAZ0008' substantially as illustrated and described herein.

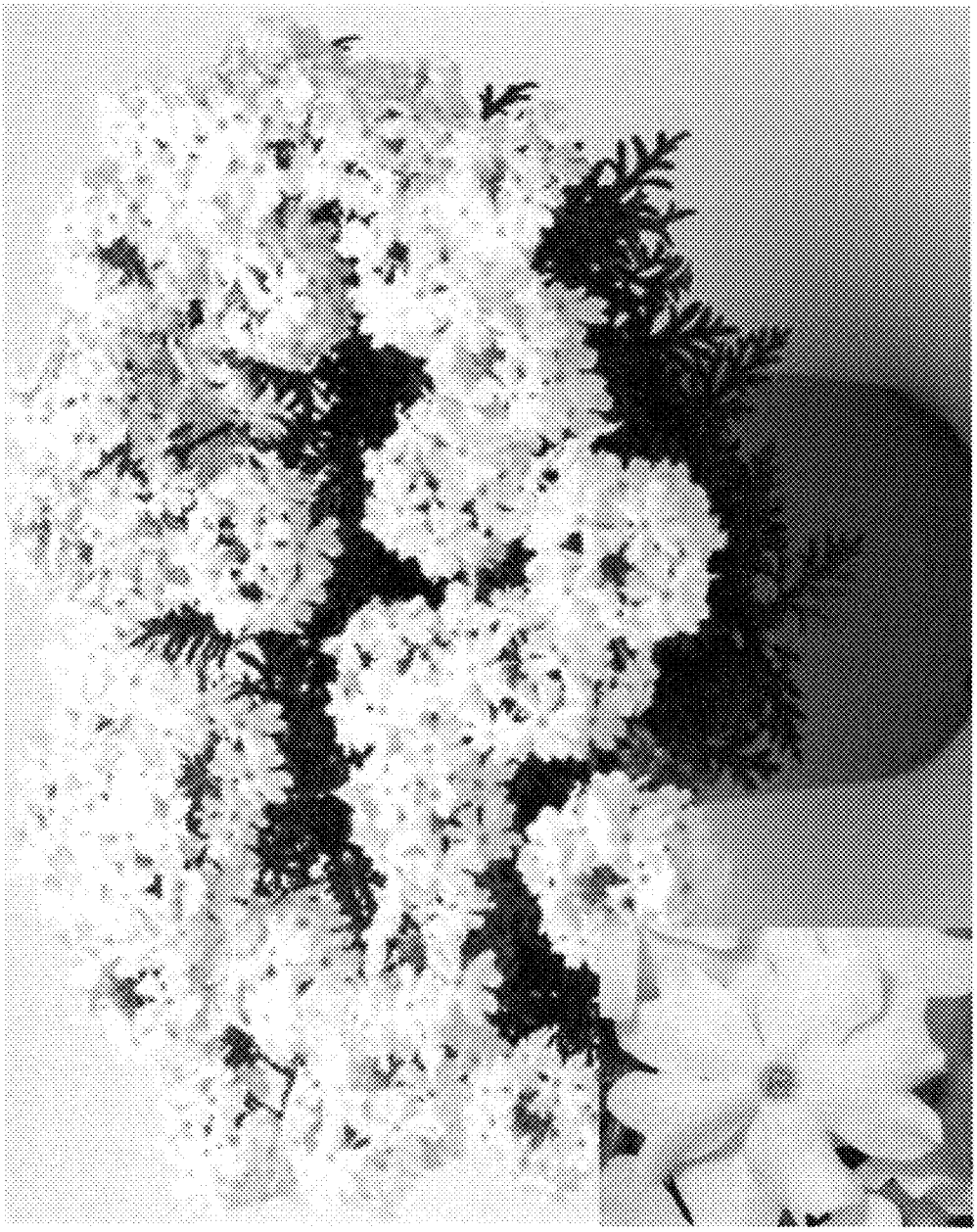

* * * * *